United States Patent [19]
Taylor et al.

[11] Patent Number: 5,240,811
[45] Date of Patent: Aug. 31, 1993

[54] PHOTOGENERATED POLYCARBODIIMIDES FROM POLY(TETRAZOLE-5-THIONES) AND USE IN THE PREPARATION OF COATINGS AND DEEP-UV PHOTORESISTS

[75] Inventors: James W. Taylor, South Charleston; David R. Bassett, Charleston, both of W. Va.

[73] Assignee: OCG Microelectronic Materials, Inc., Cheshire, Conn.

[21] Appl. No.: 684,785

[22] Filed: Apr. 15, 1991

[51] Int. Cl.$^5$ .................. G03F 7/038; G03F 7/004
[52] U.S. Cl. .................. 430/270; 430/910; 522/112
[58] Field of Search ............. 430/270, 910; 522/112

[56] References Cited

U.S. PATENT DOCUMENTS

| | | |
|---|---|---|
| 4,104,070 | 8/1978 | Moritz et al. |
| 4,487,964 | 12/1984 | Watson, Jr. et al. |
| 4,629,679 | 12/1986 | Uchida et al. ............ 430/910 X |
| 4,820,863 | 4/1989 | Taylor. |

FOREIGN PATENT DOCUMENTS

| | | | |
|---|---|---|---|
| 0247756 | 7/1987 | German Democratic Rep. ........................ 430/270 |
| 2-118643 | 5/1990 | Japan ........................ 430/270 |

Primary Examiner—Cynthia Hamilton
Attorney, Agent, or Firm—William A. Simons

[57] ABSTRACT

Photoresist formulations and coatings are provided which contain a polymer having pendant tetrazole-5-thione groups which upon exposure to ultraviolet light decompose to carbodiimides and thereby providing means for crosslinking the base polymer to provide high resolution and thermal stability.

7 Claims, No Drawings

PHOTOGENERATED POLYCARBODIIMIDES FROM POLY(TETRAZOLE-5-THIONES) AND USE IN THE PREPARATION OF COATINGS AND DEEP-UV PHOTORESISTS

BACKGROUND OF THE INVENTION

1. Field of the Invention

This invention relates in general to photogenerated polycarbodiimides obtained from poly(tetrazole-5-thiones). In another aspect, this invention is directed to the photogeneration of polycarbodiimides and their use in coatings and photoresists. In a further aspect the invention relates to novel, polymerizable tetrazole-5-thione, the polymers prepared therefrom, and certain multifunctional tetrazole-5-thiones. In a still further aspect, the invention is directed to photogenerated polycarbodiimides which are useful as crosslinking agents for polymers containing carboxylic acid groups.

2. Description of the Related Art

The trend in electronics is toward even higher resolution for imagining techniques, both in integrated circuits and in printed circuit boards. At the same time processing technologies (plasma treatments, solder contacts) require higher thermal stability. One approach to thermal stability is through cross-linking of the resin used in the imaging step. In general this requires a radiation treatment after development of the image or the use of a negative (crosslinking) resists. Negatives have had the disadvantage of requiring solvent development of the uncrosslinked portion of the resist film. However, solvents generally swell the cross-linked portion resulting in a loss of resolution. Moreover, the use of organic solvents creates undesirable environmental problems. Accordingly, an aqueous developable negative resist would avoid the problem of swelling and reduce solvent emissions as well.

Photoresists are photosensitive materials which change their solubility after exposure to light. They are typically novolac resins which have DANQ (diazonaphthoquinone) sensitizers attached to the polymer backbone or added to the resist formulation. DANQ sensitizers act as inhibitors to decrease the solubility of the photoresist in basic aqueous solutions. Irradiation of films through a mask causes the formation of indenecarboxylic acid photo-products which renders the novolac resist (in the exposed areas) soluble in aqueous base. During development, preferential dissolution of the photoresist in the irradiated areas results in a positive image.

Polycarbodiimides are excellent crosslinkers for a variety of functional polymers containing carboxylic acid or hydroxyl moieties. They are particularly effective at low temperatures and accordingly are useful for crosslinking carboxylic acid-containing polymers.

Prior to the present invention, it was known that if carbodiimides are added to photoresist formulations, negative images can obtained. When, for example, N,N'-dicyclohexyl carbodiimide is added to a novolac photoresist, it reacts reversibly with novolac hydroxyls to produce isoureas. Isoureas are "blocked" reactive agents which deactivate indenecarboxylic acid photo-products in the irradiated areas during postbake. Since the carboxylic acid groups are deactivated in the irradiated areas, the solubility in these areas are greatly reduced. After postbake, the resist is flood exposed to convert the remaining photoactive compound to indenecarboxylic acid groups; development then gives a negative image of the mask. Since this chemistry effects the solubility of the resist and does not appear to crosslink the resist in the irradiated areas, no increase in the thermal stability of the images is observed.

Since the presence of carbodiimides were shown to be useful in photoresist formulations, a study was undertaken to determine if carbodiimides could be generated in situ. Accordingly, tetrazole-5-thiones and polymers containing pendant tetrazole-5-thione groups were prepared and evaluated for their effectiveness as a source from which carbodiimides, both in monomeric and polymeric form, could be photogenerated.

SUMMARY OF THE INVENTION

In its broad aspect, the present invention is directed to poly(tetrazole-5-thiones) and their use in photoresist formulations and coatings. The liquid, photoresist formulation of the present invention containing the poly(tetrazole-5-thiones) are comprised of:

(a) a water soluble, transparent, resin containing carboxyl and/or phenolic hydroxyl groups and having a molecular weight of from about 10,000 to about 100,000, and (b) a photoactive compound in the form of a polymeric compound containing a plurality of pendant tetrazole-5-thione groups and wherein at least some of said groups decompose to carbodiimide groups when irradiated with UV light.

By exposure to UV light, photogenerated polycarbodiimides are formed in situ and serve as effective crosslinking agents. The invention is also directed to novel, polymerizable tetrazole-5-thiones, the polymers obtained therefrom as well as certain multi-functional tetrazole-5-thiones and processes for preparation. In one preferred aspect, the invention is directed to liquid dual-tone photoresist formulations containing polycarbodiimides, and to a process for improving the stability as well as enhancing the resolution of images prepared using such formulations.

DESCRIPTION OF THE PREFERRED EMBODIMENTS

Although polycarbodiimides have been evaluated for use in photoresist formulations, and were found to possess effective crosslinking properties, they did not possess the exceedingly high degree of formulation stability required when such formulations were stored for extended periods of time. While their performance was generally exemplary, the high standards set for photoresist formulations require an even higher degree of stability than that obtainable when polycarbodiimides were present.

Accordingly, as indicated above, since carbodiimides were shown to be useful in photoresist formulations, an investigation was made to determine if carbodiimides could be generated in situ and thereby avoid any problems with respect to the stability of photoresist formulations.

When tetrazole-5-thiones are irradiated at 254 nm, it was noted that they decompose to form carbodiimides. Additionally, tetrazole-5-thiones provide the photochemistry necessary for single-layer deep-UV photoresists. For tetrazole-5-thiones, where alkyl (saturated) moieties are attached to the tetrazole-5-thione ring, their molar absorptivities and quantum yields of decomposition (in PMMA) at 254 nm are approximately 12000 L/molar-cm (Log$\epsilon$=4.08) and 0.015, respectively. For tetrazole-5-thiones, where a p-bromophenyl or phenyl moiety is attached to the tetrazole-5-thione ring, their molar absorptivities are 4,827 L/molar-cm and 5,767 L/molar-cm, respectively, with quantum yields between 0.021 and 0.025. Calculations based on the quantum yield and molar absorptivity of a model tetrazole-5-thione indicate that high molecular weight poly(tetrazole-5-thiones) and poly(methylmethacrylate-co-methacrylic acids) or poly(vinyl phenols) are necessary for deep-UV photoresist with photosensitivities less than 100 mJ/cm$^2$.

The preparation of tetrazole-5-thiones, and their conversion to carbodiimides using a typical tetrazole-5-thione is shown below:

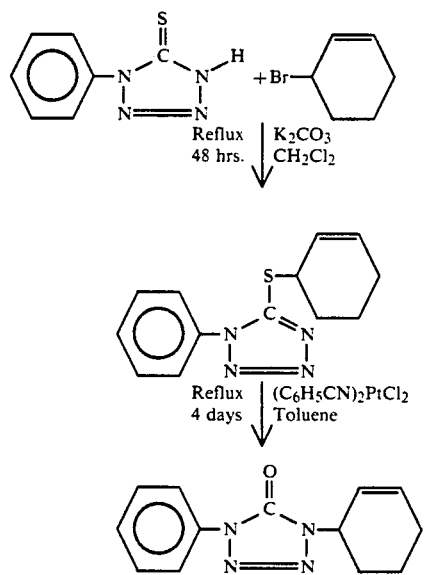

It is known that exposure to 254 mm radiation decomposes selected tetrazole-5-thiones (dissolved in acetonitrile) to carbodiimides:

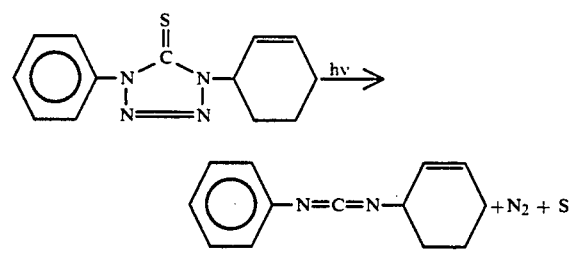

For the phenyl derivative (shown above), all of the tetrazole-5-thione decomposed in 30 hours to produce the corresponding carbodiimide in 74% yield.

It is well known that for photochemistry to occur at a given wavelength, a compound must absorb at that wavelength; thus, it was of interest to examine the absorption characteristics of a variety of tetrazole-5-thiones.

In the present invention, it has been observed that both monomeric tetrazole-5-thiones and polymers having pendant tetrazole-5-thione groups can be utilized as a source of carbodiimides. For example, poly(tetrazole-5-thiones) of the following recurring unit have been prepared which decompose when irradiated with UV light to a polymer with the same polymeric backbone but with pendant carbodiimide groups in place of the tetrazole-5-thione groups.

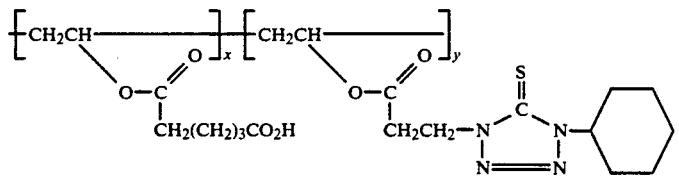

The poly(tetrazole-5-thiones) of which the above formula is one illustration, are prepared by the polymerization of vinyl ester monomers of certain tetrazole-5-thiones. These vinyl esters are themselves novel compositions of matter and are represented by the formula:

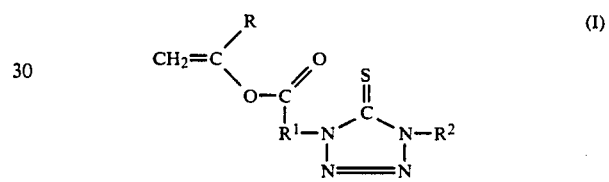

wherein R represents hydrogen or lower alkyl; $R^1$ represents a lower alkylene group, and $R^2$ represents an aliphatic, cycloaliphatic or aromatic group.

These compounds are conveniently prepared by the reaction of a tetrazole-5-thione compound with a compound containing a polymerizable group which is unreactive during formation of the ester. The following reaction is illustrative:

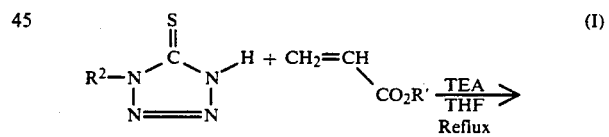

Preferred compounds are those wherein R is hydrogen or methyl, $R^1$ is ethylene or propylene and $R^2$ is alkyl, cycloalkyl, aryl, aralkyl, or alkaryl. The $R^1$ and $R^2$ may optionally be substituted with alkoxy, alkoxycarbonyl, chloro, bromo, nitro, cyano or tri (lower alkyl) silyl groups.

The reaction is conveniently conducted in an inert, organic solvent, at a temperature of from about 40° to about 140° C., and more preferably from about 500° to about 70° C. Pressure is not necessarily critical, and the reaction can be effected at atmospheric pressure or at pressures above or below atmospheric.

The mole ratio of reactants can vary from about 1 to about 4, and more preferably from about 1 to about 2.

As indicated, the reaction is conducted in an inert, organic solvent or mixtures thereof and which includes, but is not limited to, solvents such as tetrahydrofuran, dioxane, acetonitrile, and the like.

The reactants employed in preparing the vinyl ester of the tetrazole-5-thiones of formula I above, include both acrylate esters and tetrazole-5-thiones.

Illustrative acrylates include, but are not limited to, compounds such as, vinyl esters of acrylic acid, vinyl esters of metacrylic acid, isopropenyl esters of acrylic acid, propenyl esters of acrylic acid, isopropyl esters of acrylic acid, propenyl esters of methacrylic acid, allylesters of acrylic acid, allyl esters of methacrylic acid and the like.

The tetrazole-5-thione component employed in preparing the vinyl esters include, among others, 1-cyclohexyl tetrazole-5-thione, 1-methyl tetrazole-5-thione, 1-t-butyl tetrazole-5-thione, 1-n-butyl tetrazole-5-thione, 1-phenyl tetrazole-5-thione, 1-benzyl tetrazole-5-thione,1-(p-nitro phenyl)tetrazole-5-thione, 1-(p-bromo phenyl)tetrazole-5-thione, 1-(m-bromo benzyl)tetrazole-5-thione,1-(p-cyano phenyl)tetrazole-5-thione, 1-isopropyl tetrazole-5-thione, and the like.

As previously indicated, the invention also includes multifunctional thione compounds which are conveniently prepared by the reaction of a multifunctional monomer with tetrazole-5-thiones. These compounds have the following formula:

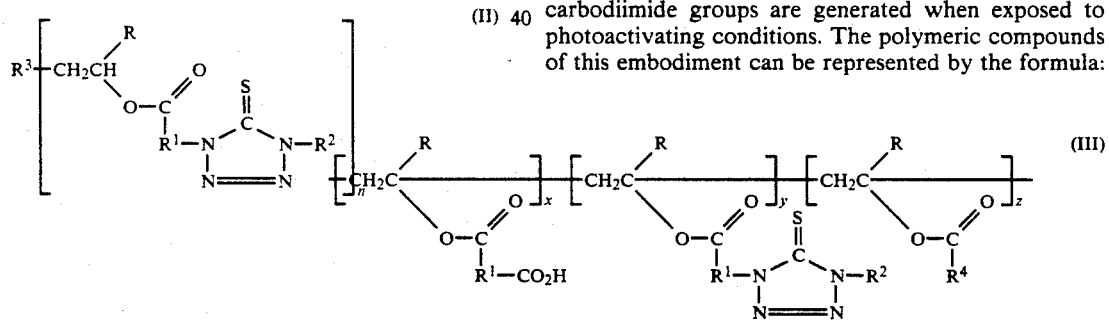

(II)

wherein $R^1$ and $R^2$ have the same values as indicated for the compounds of formula I, $R^3$ is the residue of a multifunctional monomer and N has a value of from 2 to 5.

The multifunctional tetrazole-5-thione compounds are prepared by the reaction of a monomeric compound containing from 2 to 5 unsaturated groups which are capable of undergoing a Michael's reaction with a tetrazole-5-thione.

Illustrative monomeric compounds include among others, dipentaerythritol monohydroxypentaacrylate, trimethylolpropane trimethacrylate, pentaerythritol tetraacrylate, ethoxylated trimethylolpropane triacrylate, ethyl glycol diacrylate, trimethylolpropane triacrylate, and the like.

The tetrazole-5-thione starting materials are the same as those used in the preparation of the aforementioned novel vinyl esters of formula (I).

For example, the reaction of a tetrazole-5-thione with pentaerythritol provides a multifunctional tetrazole-5-thione of the following formula:

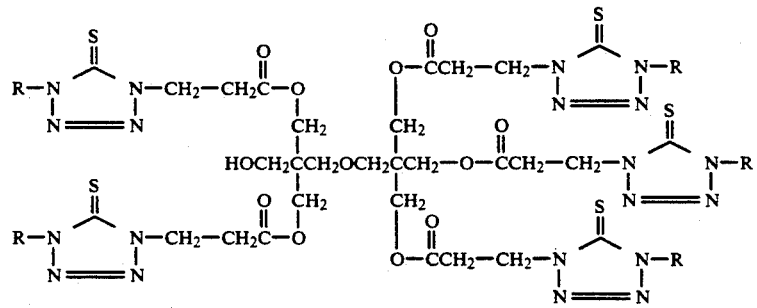

wherein R can be cyclohexyl (see Example 2) or phenyl (see Example 3)

The reaction is conveniently conducted in an inert, organic solvent at a temperature of from about 40° to about 140° C., and more preferably from about 50° to about 70° C. Pressure is not necessarily critical and the reactions can be effected at atmospheric pressure or at pressures above or below atmospheric.

The mole ratio of reactants can vary from about 1 to about 4, and more preferably from about 1 to about 2.

As indicated, the reaction is conducted in an inert, organic solvent or mixture thereof and which includes, but is not limited to, solvents such as tetrahydrofuran, dioxane, acetonitrile, and the like.

In a further embodiment the invention is directed to polymeric compounds containing pendant tetrazole-5-thione groups from which the corresponding pendant carbodiimide groups are generated when exposed to photoactivating conditions. The polymeric compounds of this embodiment can be represented by the formula:

(III)

wherein R, $R^1$ and $R^2$ are as previously indicated and $R^4$ represents alkyl, aryl and cycloalkyl and have a molecular weight of from about 2,000 to about 100,000. For use in photoresistant formulations, it is preferred that the molecular weight of the polymeric compound be from about 4,000 to about 60,000. For other applications, the molecular weights can be above or below these ranges.

Also for photoresist formulations, the ratio of X and Y will usually be in the range of from about 0.23 to about 0.43 for X and from about 0.77 to about 0.56 for Y. Z can have a value of zero for photoresist applications. For other applications, the values of X, Y and Z can vary outside of the ratios and both X and Z can have values of from zero up to about 0.9, and Y a value of from 0.01 to 1.0 (when X and Z are zero).

The value of R, R¹ and R² are the same as previously indicated.

The invention also encompases the polymeric compounds of formula (III) above wherein some, but not all, of the pendant tetrazole-5-thione groups have been converted to the corresponding carbodiimide group. While polycarbodiimides are known, there is no disclosure in the literature of polymeric compounds containing both pendant tetrazole-5-thione groups and pendant carbodiimide groups on the same chain.

The starting materials for preparing the poly(tetrazole-5-thiones) of formula (III) above are the tetrazole-5-thiones of formula (I) and one or more vinyl esters such as the vinyl adipates of the formula:

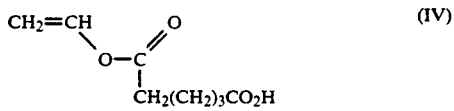

(IV)

wherein R and R¹ are as previously defined.

The polymerization reaction is conveniently conducted in an inert, organic solvent at a temperature of from about 60 to about 180° C., and more preferably from about 130° to about 150° C. Pressure is not necessarily critical and the reaction can be effected at atmospheric pressure or at pressures above or below atmospheric.

The mole ratio of reactants can vary as previously discussed.

As indicated, the reaction is conducted in an inert, organic solvent or mixtures thereof and which includes, but is not limited to, solvents such as propylene glycol monomethyl ether acetate (PM Acetate), ethyl lactate, cyclopentanone, amyl acetate, and the like.

Initiators can employed to effect polymerization. Typical initiators include but are not limited to tert-butyl peroxybenzoate, benzoyl peroxide, azobisisobutyronitrile, and the like.

The polymeric compounds of this invention, either above or in admixture with the monomeric or multifunctional-5-thione compounds of formulas (I) or (II), are particularly suitable for use in photoresist formulations. By utilizing the tetrazole-5-thione compounds which are stable in photoresist formulations which might be stored for periods of time, the desired crosslinking function of the carbodiimide remains dormant until needed. Then, upon exposure to UV light, the desired polycarbodiimide is generated.

Polycarbodiimides are effective crosslinking agents at low temperatures for functional polymers containing carboxylic acid and/or hydroxyl moieties. The polymers containing the functional groups which are used in the photoresist formulations and polymers and copolymers of monomeric compounds containing a polymerizable groups, preferably a vinyl group, and at least a carboxyl or hydroxyl group or a group easily convertible to carboxyl or hydroxyl. Illustrative polymers are those prepared by the polymerization of monomeric compounds such as vinyl phenols, vinyl esters, and the like.

For photoresist applications, the cross-linkable polymeric compounds are characterized by a molecular weight of from about 10,000 to about 100,000.

The concentration of the tetrazole-5-thione compound in the photoresist formulation should preferable be such that upon exposure to light, a sufficient number of the pendant tetrazole-5-thione groups are converted to corresponding carbodiimide to effect crosslinking of the formulation.

In practice, it has been found that in a photoresist formulation, the poly(tetrazole-5-thione) is present in an amount of from about 0.01 to about 20 percent by weight, and more preferably from about 0.1 to about 15 percent by weight based on the total weight of the formulation. Other compounds normally used may also be present in the formulation as desired.

As previously indicated, conversion of the tetrazole-5-thione group(s) to the corresponding carbodiimide group(s) is effected by exposure of the tetrazole-5-thione compound to photoactivating conditions. In practice, photogeneration of the carbodiimide moieties from the corresponding tetrazole-5-thiones, is conveniently effected by the use of ultraviolet light of the proper wave length.

It has been observed that photogeneration of the desired carbodiimides can be achieved by exposing the tetrazole-5-thione compound to UV light having a wavelength between about 230 to about 366 nm.

Although the tetrazole-5-thione compounds of the invention are particularly useful in photoresist formulations, if desired, the tetrazole-5-thione compounds of this invention as illustrated by the compounds of formulas I, II, and III, are also useful for crosslinking other formulations besides those utilized for photoresist applications. For example, the poly(tetrazole-5-thione) can be used cure coating compositions wherein the entire coating formulation is exposed to UV-light to generate polycarbodiimides and thereby cross-link polymeric compounds containing carboxylic and/or hydroxyl groups.

The following examples are illustrative of the invention:

EXAMPLE 1

Preparation of 1-Cyclohexyltetrazole-5-thione

To a 2000 ml round-bottomed flask equipped with a condenser were charged 1415 g of distilled water, 100.0 g (0.7080 mole) of cyclohexyl isothiocyanate, 69.04 g (1.062 moles) of sodium azide and two boiling chips. The reactants were refluxed for 8 hours, then the reaction solution is filtered to remove the by-product, N, N'-dicyclohexyl thiourea (11.94 g, dry weight). The filtrate was extracted two times with 750 ml portions of methylene chloride to remove unreacted cyclohexylisothiocyanate, and the pH was adjusted to from 10.95 to 2.94 with 79.2 g of concentrated hydrochloric acid. The precipitated product was filtered, washed with water, and crystallized from ethanol and water. TLC (96% chloroform, 4% ethanol) over silica gel showed the product to be pure ($R_f$=0.146). After drying overnight under vacuum at 30°-35° C., 101.85 g of product were obtained. Yield, 78.1%; m.p. 136°-137° C.; UV, lambda$_{max}$=248 nm (in methanol); mass spec. 185 (CI); IR (KBr), 3057 cm$^{-1}$; $^{13}$C NMR, 164.5 ppm ($\delta$), (acetone-$d_6$) (C=S); $^1$H NMR ($\delta$), (acetone-$d_6$) 1.21-2.1 (mult), 4.5-4.7 (mult) ppm.

EXAMPLE 2

Preparation of the dipentaerythritol monohydroxypenta-4(3-propionate-1-cyclohexyltetrazole-5-thione To a 2000 ml round-bottomed flask equipped with a condenser, thermometer, mechanical stirrer, and nitrogen inlet tube were charged 142.33 g (0.7724 mole) of 1-cyclohexyltetrazole-5-thione, 1293 g of tetrahydrofuran, 73.65 g (0.1400 mole) of dipentaerythritol monohydroxypentaacrylate, and 82.10 g (0.8111 mole) of triethyl amine. The mixture was stirred at room temperature until a clear homogeneous solution was obtained, then the solution refluxed. After 7 days, IR analysis of the acrylate double absorption showed that the reaction was 93% over. The reaction was stopped, then 250 ml of methylene chloride added to the reaction solution.

Residual 1-cyclohexyltetrazole-5-thione was extracted from solution washing the organic phase with two 170 ml portions of a water solution containing 5% dimethylethanol amine. To the organic phase was added 170 ml of water, the water phase neutralized to a pH of 6. The neutralized water phase was separated from the organic phase, then the organic phase washed twice with 170 ml portions of water. The organic phase was then dried over 4% molecular sieves. A roto-evaporator was then used to remove the organic solvent. A crude product yield of 188 g was obtained (yield=82%). Purification by flash chromatography (silica gel; eluant, methylene chloride) gave 55 g of a viscous liquid. A TLC of the product (silica gel; eluant, 84% chloroform, 16% ethanol) showed that the product was pure ($R_f$=0.824). Yield, 26%., UV, lambda$_{max}$=251 nm (in tetrahydrofuran), IR (neat), 1725 cm$^{-1}$; $^{13}$C NMR 163 ppm ($\delta$), (acetone-d$_6$) (C=S).

EXAMPLE 3

Preparation of the dipentaerythritol monohydroxypenta-4(3-propionate)-1-phenyltetrazole-5-thione The preparation of the five-functional tetrazole-5-thione was similar to Example 2. Purification by flash chromatography (silica gel; eluant, methylene chloride) gave 55 g of a viscous liquid. A TLC of the product (silica gel; eluant, 86% chloroform, 14% ethanol) showed that the product was essentially pure ($R_f$=0.747). Yield, 28%; UV, lambda$_{max}$=266 nm (in tetrahydrofuran), IR (neat), 1725 cm$^{-1}$; 1600 cm$^{-1}$ $^{13}$C NMR 164 ppm ($\delta$), (acetone-d$_6$) (C=S).

EXAMPLE 4

Preparation of the vinyl ester of 1-cyclohexyl-4(3-propionic acid) tetrazole-5-thione To a 100 ml round-bottomed flask equipped with a condenser thermometer, mechanical stirrer, and nitrogen inlet tube were charged 52.6 g (0.2857 mole) of 1-cyclohexyltetrazole-5-thione from Example 1, 361 g of tetrahydrofuran, 25 00 g (0.2548 mole) of vinyl acrylate, and 27.34 g (0.2701 mole) of triethyl amine. After 13 days at reflux, IR analysis showed that the acrylate double absorption at 1626 cm$^{-1}$ had disappeared, and that the reaction was complete. Tetrahydrofuran was removed using a roto-evaporator. To the crude product was added 100 ml of methylene chloride, then the organic phase was washed with a water solution containing 5% dimethylethanol amine until the 1-cyclohexyltetrazole-5-thione was removed. To the organic layer was then added 63 ml of water, and the water phase neutralized to a pH of 7 using 10% aqueous hydrogen chloride. The layers were then separated, and the organic layer was then dried over 4 Å molecular sieves. Removal of the methylene chloride gave a viscous liquid. The material was purified on a column of silica gel. TLC analysis showed the product to be pure. Yield, 44%.; UV, lambda$_{max}$=251 nm (in tetrahydrofuran); mass spec. 283 (CI); IR (solvent, tetrahydrofuran), 1760 cm$^{-1}$, 1645 cm$^{-1}$; $^{13}$C NMR 164.0, 167.9 ppm ($\delta$), (tetrahydrofuran-d$_8$) (C=S, and C=O).

EXAMPLE 5

Preparation of the poly(tetrazole-5-thione) Containing a Cyclohexyl Moiety and 26% Monovinyl Adipate.

To a 50 ml round-bottomed flask equipped with a stirrer, nitrogen purge, and condenser were charged 4.7 g (0.086 moles) of vinyl ester of 1-cyclohexyl-4(3-propionic acid) tetrazole-5-thione, 170 g monovinyl adipate, and 15 g of PM Acetate. The reactor was purged with nitrogen gas, heated to 130° C., then 0.15 g of the initiator, t-butyl peroxybenzoate, was charged to the reactor. After 5 hours, the contents of the reactor were cooled, and the PMA removed from polymer using a roto-evaporator. The polymer was dissolved in 11 g of acetone, then precipitated into 400 ml of water. The polymer was vacuum dried overnight at 35° C. Polymer yield, 95%; UV, lambda$_{max}$=254 nm (in tetrahydrofuran); IR 1737 cm$^{-1}$, 1707 cm$^{-1}$ (film, cast from methylene chloride); GPC, $M_n$=3620 g/mole, $M_w$=7660 g/mole.

EXAMPLE 6

Preparation of the Poly(tetrazole-5-thione) Containing a Cyclohexyl Moiety and 12% Monovinyl Adipate.

To a 50 ml round-bottomed flask equipped with a stirrer, nitrogen purge, and condenser were charged 5.0 g (0.086 moles) of the vinyl ester of 1-cyclohexyl-4(3-propionic acid) tetrazole-5-thione, 0.70 g monovinyl adipate, and 15 g of PM Acetate. The reactor was purged with nitrogen gas, heated to 130° C., then 0.15 g of the initiator, t-butyl peroxybenzoate, was charged to the reactor. After 5 hours, the contents of the reactor were cooled, and the PMA removed from polymer using a roto-evaporator. The polymer was dissolved in 21 g of tetrahydrofuran, then precipitated into 300 ml of water. The polymer was vacuum dried overnight at 35° C. Polymer yield 44%; UV, lambda$_{max}$=254 nm (in tetrahydrofuran); IR 1737 cm$^{-1}$, 1709 cm$^{-1}$ (film, cast from tetrahydrofuran); GPC, $M_n$=3700 g/mole, $M_w$=9500 g/mole.

EXAMPLE 7

Preparation of a Monodispersed Polymer Containing 26% Methacrylic Acid MMA/MAA;74/26

To a dried round-bottomed flask equipped with a stirrer (mechanical), nitrogen purge, and condenser were charged 317 g of tetrahydrofuran, methyl trimethyl silyl dimethyl ketene acetal and 3.0 ml of a 0.1M solution of tri(dimethylamino)sulfur-(trimethyl silyl)difluoride in acetonitrile. The monomer solution composed of 192.38 g of methyl methacrylate, and 125 g of trimethylsilyl methacrylate was fed in. The feed is kept at such a rate as to keep the reaction temperature less than 28° C. Polymerization was monitored by determining the conversion to polymer. After 18 hours the conversion to polymer was 84%, and an additional 3.0 ml of tri(dimethylamino)sulfur-(trimethylsilyl) difluoride solution was added to the reaction pot over a 30 minute period. After an additional five hours the polymerization was complete. To the polymer solution was added 44 g of a 50% water-THF solution, and the solution heated for one hour at 60° C. The polymer was precipitated by slowly dropping it into water (15 parts water to 1 part polymer solution, by volume). The polymer was filtered then vacuum dried overnight at 80° C. Yield, 258 g; GPC, $M_n=21,533$, $M_w=24,158$.

EXAMPLE 8

Formulation of a Deep UV Negative Photoresist Using Poly(vinyl phenol) and a Five Functional tetrazole-5-thione To a small screw cap bottle were charged 2.06 g of poly(vinyl phenol) (Mw=30,800), 14 g of 2-methoxyethyl ether, and an 0.772 g solution of the five functional tetrazole-5-thione (from Example 1) at 40 weight percent in PM Acetate. The solution was filtered through a 0.2 micron filter.

EXAMPLE 9

Demonstration of Negative Deep UV Images

A sample of the photoresist formulation from Example 8 was spun over a silicon oxide wafer then soft baked on a hot plate at 90° C. for one minute. A dry film thickness of 0.7 microns was obtained. The film was exposed at 880 mJ/cm$^2$ through a contact mask using an Oriel Deep UV source, then postbaked on a hot plate at 150° C. for 3 minutes. The image was obtained using a sodium hydroxide developer (1.5 weight percent NaOH in water).

EXAMPLE 10

Demonstration of Negative Deep UV Images

A sample of the photoresist formulation from Example 8 was spun over a silicon oxide water then soft baked on a hot plate at 90° C. for one minute. A dry film thickness of 0.7 microns was obtained. The film was exposed at 1100 mJ/cm$^2$ through a contact mask using an Oriel Deep UV source, then postbaked on a hot plate at 160° C. for 4.3 minutes. The image was obtained using KTI 934 developer diluted with deionized water (2 parts KTI 934 to 1 part water). (KTI developer is sold by KTI, a subsidiary of Union Carbide Chemicals and Plastics Company Inc.)

EXAMPLE 11

Demonstration of Negative Deep UV Images

A sample of the photoresist formulation from Example 8 was spun over a silicon oxide wafer than soft baked on a hot plate at 90° C. for one minute. A dry film thickness of 0.7 microns was obtained. The film was exposed at 660 mJ/cm$^2$ through a contact mask using an Oriel Deep UV source, then postbaked on a hot plate at 160° C. for 3 minutes. The image was obtained using KTI 934 developer diluted with water and 2-methoxyethyl ether (2 parts KTI 932 to 1 part water and 0.3 part 2-methoxyethyl ether).

EXAMPLE 12

Formulation of a Deep UV Negative Photoresist Using Poly(methyl methacrylate-co-methacrylic acid) and a Five Functional Tetrazole-5-thione To a small screw cap bottle were charged 1.48 g of poly(methyl methacrylate-co-methacrylic acid) from Example 7, 7.35 g of 2-methoxyethyl ether, and a 0.75 g solution of the five functional tetrazole-5-thione (from Example 2) at 40 weight percent in PM Acetate. The solution was filtered through at 0.2 micron filter.

EXAMPLE 13

Demonstration of Negative Deep UV Images

A sample of the photoresist formulation from Example 12 was spun over a silicon oxide wafer then soft baked on a hot plate at 90° C. for one minute. A dry film thickness of 0.9 micron was obtained. The film was exposed at 1100 mJ/cm$^2$ through a contact mask using an Oriel Deep UV source, then postbaked on a hot plate at 150° C. for 3 minutes. The image was obtained using KTI 950.

EXAMPLE 14

Formulation of a Deep UV Negative Photoresist Using Poly(methyl methacrylate-co-methacrylic acid) and a Five Functional Tetrazole-5-thione To a small screw cap bottle were charged 1.48 g of poly(methyl methacrylate-co-methacrylic acid) from Example 7, 7.35 g of 2-methoxyethyl ether, and an 0.925 g solution of the five functional tetrazole-5-thione (phenyl der.) (from Example 3) at 40 weight percent in PM Acetate. The solution was filtered through a 0.2 micron filter.

EXAMPLE 15

Demonstration of Negative Deep UV Images

A sample of the photoresist formulation from Example 14 was spun over a silicon oxide water then soft baked on a hot plate at 90° C. for one minute. A dry film thickness of 0.9 micron was obtained. The film was exposed at 1100 mJ/cm$^2$ through a contact mask using an Oriel Deep UV source, then postbaked on a hot plate at 160° C. for 4 minutes. The image was obtained using KTI 943 diluted with an equal volume of deionized water.

EXAMPLE 16

Formulation of a Deep UV Negative Photoresist Using Poly(methyl methacrylate-co-methacrylic acid) and a Poly(tetrazole-5-thione)

To a small screw cap bottle were charged 0.89 g of poly(methyl methacrylate-co-methacrylic acid) from Example 7, 5.11 g of 2-methoxyethyl ether, and an 0.13 g poly(tetrazole-5-thione) from Example 6. A homogeneous solution was obtained and was filtered through a 0.2 micron filter.

EXAMPLE 17

Demonstration of Negative Deep UV Images

A sample of the photoresist formulation from Example 16 was spun over a silicon oxide wafer then soft baked on a hot plate at 90° C. for one minute. A dry film thickness of 0.9 micron was obtained. The film was exposed at 690 mJ/cm$^2$ through a contact mask using an Oriel Deep UV source, then postbaked on a hot plate at 140° C. for 5 minutes. The image was obtained using KTI 934. An image was obtained, but scumming was observed.

EXAMPLE 18

Formulation of a Deep UV Negative Photoresist Using Poly(vinyl phenol) and a Poly(tetrazole-5-thione)

To a small screw cap bottle were charged 2.0 g of poly(vinyl phenol), Mw=30,800 (purchased from Hoechst Calanese), 9.7 g PM Acetate, and an 0.20 g poly(tetrazole-5-thione) from Example 5. A homogeneous solution was obtained and was filtered through a 0.2 micron filter.

EXAMPLE 19

Demonstration of Negative Deep UV Images

A sample of the photoresist formulation from Example 18 was spun over a silicon oxide wafer then soft baked on a hot plate at 90° C. for one minute. A dry film thickness of 1.3 micron was obtained. The film was exposed at 500 mJ/cb$^2$ through a contact mask using an Oriel Deep UV source, then postbaked on a hot plate at 150° C. for 2 minutes. The image was obtained using KTI 934 to 1 part water).

EXAMPLE 20

Formulation of a Deep UV Negative Photoresist Using Poly(vinvl phenol) and a Poly(tetrazole-5-thione)

To a small screw cap bottle were charged 6.0 g of poly(vinyl phenol), Mw=30,800 (purchased from Hoechst Calanese), 40 g PM Acetate, and an 0.63 g poly(tetrazole-5-thione) from Example 5. After a homogeneous solution was obtained, two drops of the surfactant FC-430 (10 wt % in 2-methoxyethyl ether) were added. A homogeneous solution was obtained and was filtered through a 0.2 micron filter. The total solids of the photoresist was 14.2 weight percent.

EXAMPLE 21

Demonstration of Negative Deep UV Images

A sample of the photoresist formulation from Example 20 was spun over a silicon oxide wafer then soft baked on a hot plate at 80° C. for one minute. A dry film thickness of 1.0 micron was obtained. The film was exposed at 600 mJ/cm$^2$ using a Canon FPA 4500 UV stepper then the film was postbaked on a hot plate at 160° C. for 3 minutes. One micron equal lines and spaces were obtained using KTI 934. The developer was diluted with deionized water (2 parts KTI 934 to 1 part water).

EXAMPLE 22

Preparation of the vinyl ester of 1-phenyl-4(3-propionic acid) tetrazole-5-thione To a 1000 ml round-bottomed flask equipped with a condenser thermometer, mechanical stirrer, and nitrogen inlet tube were charged 50.92 g (0.2857 mole) of 1-phenyltetrazole-5-thione (Available from Aldrich), 361 g of tetrahydrofuran, 25.00 g (0.2548 mole) of vinyl acrylate, and 27.34 g (0.2701 mole) of triethyl amine. After 6 days at reflux, IR analysis showed that the acrylate double absorption at 1626 cm$^{-1}$ had disappeared, and that the reaction was complete. Work-up was similar to Example 4 Yield, 61%.; m.p. 49°-51° C.; UV, lambda $_{max}$=265 nm (in tetrahydrofuran); IR (KBr), 1746 cm$^{-1}$, 1645 cm$^{-1}$, mass spec. 277 (CI); $^{13}$C NMR, 164.2, 163.2 (δ) (C=S, C=O), (acetone-d$_6$).

EXAMPLE 23

Preparation of the poly(tetrazole-5-thione) containing a phenyl group

To a 50 ml round-bottomed flask equipped with a stirrer, nitrogen purge, and condenser were charged 5.0 g of the vinyl ester of 1-phenyl-4(3-propionic acid) tetrazole-5-thione, and 15.7 g of PM Acetate. The reactor was purged with nitrogen gas, heated to 120° C., then 0.269 g of the initiator, t-butyl peroxybenzoate, dissolved in 7.4 g of PM Acetate was fed into the reactor over a 4 minute period. After 7 hours, the contents of the reactor were cooled, and the PMA removed from polymer using a roto-evaporator. IR analysis showed that the acrylate absorption at 1645$^{-1}$ has disappeared. The polymer was dissolved in tetrahydrofuran, then precipitated into water. The polymer was vacuum diried overnight at 45°-50° C. Polymer yield, 86%; UV, IR 1725 cm$^{-1}$ (film, cast from tetrahydrofuran); GPC, M$_n$=2000 g/mole, M$_w$=6000 g/mole.

EXAMPLE 24

Photodecomposition of Poly(tetrazole-5-thione) containing a phenyl group

A thin film containing 10 parts (10 microns) of the poly(tetrazole-5-thione) and 100 part poly(methyl methacrylate) was cast over a sodium chloride disc. The film was exposed using a deep-UV oriel 500W lamp for 100 seconds (0.6 mw/cm$_2$ at 254 nm). IR analysis of the exposed film showed the presence of the carbodiimide absorption at 2134 cm$^{-1}$.

Although the invention has been illustrated by the preceding examples, it is not to be construed as being limited to the materials employed therein but rather, the invention is directed to the generic area as hereinbefore disclosed. Various modifications and embodiments thereof can be made without departing from the spirit or scope thereof.

What is claimed is:

1. A liquid, photoresist formulation for the production of positive or negative images, said formulation comprised of:
   (a) a water soluble, transparent resin containing carboxyl and/or phenolic hydroxyl groups and having a molecular weight of from about 10,000 to about 100,000, and
   (b) A photoactive compound, in the form of a polymeric compound containing a plurality of pendant tetrazole-5-thione groups and wherein at least some of said groups decompose to carbodiimide groups when irradiated with UV light.

2. The formulation of claim 1 wherein the resin is a poly(vinyl phenol).

3. The formulation of claim 1 wherein the resin is a carboxylic acid-containing acrylic resin.

4. The formulation of claim 1 wherein the photoactive compound is a poly(tetrazole-5-thione).

5. The formulation of claim 1 wherein the pendant tetrazole-5-thione groups decompose to the pendant carbodiimide groups at wavelengths from about 230 to about 366 um.

6. The formulation of claim 1 wherein the polymeric compound has the formula:

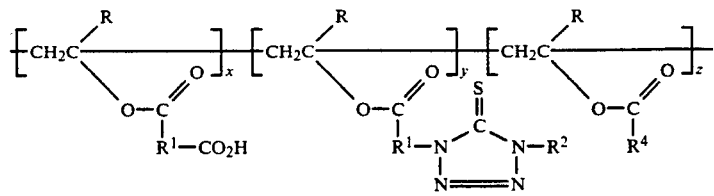

wherein each R represents hydrogen or lower alkyl, each $R^1$ represents lower alkylene, $R^2$ represents an aliphatic, cycloaliphatic or aromatic group, each $R^4$ represents alkyl, aryl or cycloalkyl, and wherein each R, $R^1$, $R^2$ and $R^4$ optionally contain substituents selected from the group consisting of alkoxy, alkoxycarbonyl, chloro, bromo, nitro, cyano and tri (lower alkyl) silyl groups, X is present in a mole ratio of from about 0.23 to about 0.43, Y is present in a mole ratio of from about 0.77 to about 0.56 and Z has a value of zero or present in a mole ratio of from about 0.1 to about 0.6; and the molecular weight of the polymeric compound is from about 2,000 to about 100,000.

7. The formulation of claim 6 wherein R is hydrogen, $R^1$ is lower alkylene and, $R^2$ is cyclohexyl.

* * * * *